United States Patent [19]  [11] 4,266,076
Gruffaz et al. [45] May 5, 1981

[54] PREPARATION OF ETHYL CARBOXYLATE

[75] Inventors: Max Gruffaz, La Mulatiere; Odile Micaelli, Lyons, both of France

[73] Assignee: Rhone-Poulenc Industries, Paris, France

[21] Appl. No.: 3,815

[22] Filed: Jan. 16, 1979

[30] Foreign Application Priority Data

Jan. 16, 1978 [FR] France ................ 78 01571

[51] Int. Cl.³ ............................................. C07C 67/04
[52] U.S. Cl. .................................................... 560/247
[58] Field of Search ................................ 560/241, 247

[56] References Cited

U.S. PATENT DOCUMENTS

| 2,006,734 | 7/1935 | Edlund | 560/247 |
| 2,224,809 | 12/1940 | Coleman | 560/247 |
| 2,551,643 | 5/1951 | Seger | 560/241 |
| 3,474,131 | 10/1969 | Schmerling | 560/247 |
| 3,907,873 | 9/1975 | Wight | 560/241 |
| 4,048,220 | 9/1977 | Cardenas | 560/241 |

FOREIGN PATENT DOCUMENTS 447461 3/1948 Canada ................................... 560/241

OTHER PUBLICATIONS

Roberts, J. Chem. Soc., Perkins Trans., 2, pp. 1183–1190 (1976).
Morin, Ind. & Eng. Chem., 43, pp. 1596–1600 (1951).
Battacharyya, J. Appl. Chem. 13, pp. 544–547 (1963).

*Primary Examiner*—Natalie Trousof
*Assistant Examiner*—Michael Shippen
*Attorney, Agent, or Firm*—Burns, Doane, Swecker & Mathis

[57] ABSTRACT

Carboxylic acids are esterified with ethylene or propylene gas, to effect the formation of ethyl or isopropyl esters, respectively, by acid catalysis in the presence of a catalytic amount of a perfluoro sulfonic acid.

6 Claims, No Drawings

4,266,076

PREPARATION OF ETHYL CARBOXYLATE

BACKGROUND OF THE INVENTION

1. Field of the Invention

The present invention relates to a novel process for the preparation of organic esters, and, more especially, relates to a process for the preparation of ethyl or isopropyl carboxylates by reacting a carboxylic acid with ethylene or propylene, respectively.

2. Description of the Prior Art

It has long been known that carboxylic acids react with and are esterified by olefins in the presence of acid catalysts. Although the advantages of this method for the synthesis of esters, compared to the conventional processes utilizing alcohols and inorganic acid catalysts in the liquid phase, were quickly recognized, such method has nevertheless remained a laboratory curiosity, notably in an ethyl carboxylate synthesis, because of certain difficulties encountered in the course of the reaction.

In fact, as has been earlier reported [*Ind. & Eng. Chem.*, 1951, 43, pages 1596–1600 and *J. Appl. Chem.*, 1963, pages 544–547], ethylene can only be esterified by a carboxylic acid, in the presence of an acid catalyst, under extremely severe conditions. These extremely harsh conditions, moreover, promote various secondary reactants, in particular polymerization reactions, which reactions compete with the esterification at the expense of the yield of the desired ester.

SUMMARY OF THE INVENTION

Accordingly, it is a major object of the present invention to provide an improved catalytic process, affording enhanced yields, for the preparation of ethyl or isopropyl esters by reacting ethylene or propylene with organic carboxylic acids.

Another object of the invention is to provide for the esterification of ethylene or propylene, which esterification is known to be difficult, in the presence of but small amounts of catalyst, by reacting ethylene or propylene with at least one carboxylic acid, in liquid phase, in the presence of a catalytic amount of at least one perfluoroalkanesulfonic acid.

According to the present invention, it has now surprisingly been shown that it is possible to facilely react ethylene or propylene with at least one carboxylic acid, in the liquid phase, and in the presence of at least one perfluoroalkanesulfonic acid in catalytic amount, to remarkably provide ethyl or isopropyl esters in good yield, under relatively mild conditions, with the result that the process can easily be scaled up to an industrial level and is broadly applicable to a variety of organic carboxylic acids.

DETAILED DESCRIPTION OF THE INVENTION

More particularly, it has now surprisingly been found that perfluorosulfonic acids of the formula $C_nF_{2n+1}SO_3H$, in which n is an integer of from 0 to 8, are efficient catalysts for the esterification of ethylene or propylene with carboxylic acids in the liquid phase.

The invention also envisages the use, as catalysts, of the aforesaid acids, either wholly or partially in the form of their lower alkyl esters having, in particular, from 1 to 4 carbon atoms in the alkyl radical, and, more particularly, wholly or partially in the form of their ethyl or isopropyl esters.

The subject reaction is preferably carried out utilizing trifluoromethanesulfonic acid, and/or its lower alkyl esters especially in light of its greater stability under the conditions of reaction.

Trifluoromethanesulfonic acid, and/or its ethyl or isopropyl esters, are especially preferred for carrying out the present invention.

The choice of carboxylic acid to be esterified, according to the present invention, will quite obviously depend on the nature of the desired ethyl or isopropyl ester. By way of examples of carboxylic acids which can be esterified within the scope of the present invention, there are mentioned: saturated or unsaturated aliphatic monocarboxylic acids which have up to 20 carbon atoms in the molecule, and which are either unsubstituted or bear substituents, especially one or more halogen atoms, in particular acetic, propionic, isobutyric, hexanoic, monochloroacetic, dichloroacetic, bromoacetic, α-chloropropionic, α-bromopropionic, acrylic and methacrylic acids. The invention also envisages the use of aromatic monocarboxylic acids and halo-derivatives thereof, in particular benzoic and toluic acids, alicyclic acids such as naphthenic acids, aliphatic dicarboxylic acids having from 3 to 6 carbon atoms in the molecule, in particular succinic and adipic acids, and aromatic dicarboxylic acids, in particular the phthalic acids.

The saturated aliphatic monocarboxylic acids having at most 10 carbon atoms in the molecule and which are substituted by a single bromine or chlorine atom in the α-position, or by more than one bromine and/or chlorine atoms, constitute a particularly valuable class of reactants to be esterified within the ambit of the invention. An acid selected from the group comprising monochloroacetic acid, dichloroacetic acid, monobromoacetic acid, dibromoacetic acid, α-chloropropionic acid, α-bromopropionic acid and α,α-dichloropropionic acid is preferably employed.

The amount of catalyst to be introduced into the reaction medium can be as little as 0.05 mol per liter of reaction mixture and, in general, there is no useful purpose in exceeding 1 mol per liter of reaction mixture. The amount of catalyst is preferably between 0.1 and 0.5 mol per liter of reaction mixture.

In accordance with the invention, ethyl or isopropyl esters are obtained by reacting ethylene or propylene gas, under pressure, with a carboxylic acid, in the liquid phase and in an essentially anhydrous medium, in the presence of at least one perfluorosulfonic acid as the catalyst.

When reacting propylene in accordance with the process of the invention, a pressure between 20 and 60 bars is particularly suitable, it being possible for the reaction temperature to vary between 100° and 200° C., and preferably between 130° and 160° C.

In order to further illustrate the present invention and the advantages thereof, the following specific examples are given, it being understood that same are intended only as illustrative and in nowise limitative.

EXAMPLES 1 to 4

Preparation of Ethyl Esters

The noted carboxylic acid and the catalyst were introduced into a 250 cm³ Hastelloy C bomb reactor. The mixture was heated to the selected temperature in an oven, with lengthwise agitation, and ethylene was then charged therein under pressure, the pressure being 40 bars. The reaction was terminated at the desired time.

The results obtained, expressed as the degree of conversion (DC) of the acid into the desired ethyl ester, and also the particular reaction conditions, are reflected in the Table I below.

The selectivity with respect to the desired ester was on the order of 100%. By way of comparison, experiments a and b were carried out with sulfuric acid as the catalyst.

TABLE I

| EXAMPLE No. | CATALYST Nature | Mol/liter | CARBOXYLIC ACID Nature | Mol | T°C. | DURATION in HOURS | DC% |
|---|---|---|---|---|---|---|---|
| 1 | $CF_3SO_3H$ | 0.324 | $CH_3COOH$ | 1.64 | 150 | 4 | 9.3 |
| a | $H_2SO_4$ | 0.925 | $CH_3COOH$ | 1.64 | 150 | 4 | 3.5 |
| 2 | $CF_3SO_3H$ | 0.323 | $CH_2Cl—COOH$ | 1.40 | 140 | 3 | 64.2 |
| b | $H_2SO_4$ | 0.963 | $CH_2Cl—COOH$ | 1.40 | 150 | 3 | 56.5 |
| 3 | $C_6F_{13}SO_3H$ | 0.1 | $CH_2Cl—COOH$ | 1.41 | 150 | 4 | 31.1 |
| 4 | $CF_3SO_3H$ | 0.113 | $CH_3CHCl—COOH$ | 1.18 | 150 | 4 | 20.0 |

EXAMPLE 5

Preparation of Isopropyl Acetate 1.66 mols of acetic acid and 0.21 mol/liter of trifluoromethanesulfonic acid were introduced in accordance with the general procedure described for the preceding examples.

The mixture was heated to 100° C. Propylene was then charged therein under a pressure of 10 bars. The reaction was terminated after four hours.

The degree of conversion of the acetic acid was 88.7% and the selectivity with respect to isopropyl acetate was on the order of 100%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the preparation of an ethyl carboxylate, in liquid phase, from ethylene under pressure and at least one carboxylic acid, the improvement which comprises conducting the esterification reaction (i) in the presence of a catalytic amount of a member selected from the group consisting of a perfluoroalkanesulfonic acid having the structural formula:

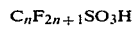

$$C_nF_{2n+1}SO_3H$$

wherein n is an integer of from 1 to 8, a lower alkyl ester thereof, and mixtures thereof; (ii) under a pressure of from about 20 to 60 bars; and (iii) at a temperature of from about 100° to 200° C.

2. The process as defined by claim 1, the perfluorosulfonic acid being trifluoromethanesulfonic acid.

3. The process as defined by claim 1, said esterification reaction being conducted in the presence of a catalytic amount of a lower alkyl ester of the perfluorosulfonic acid, said lower alkyl ester having from 1 to 4 carbon atoms.

4. The process as defined by claim 3, said lower alkyl ester being selected from the group consisting of the ethyl ester and the isopropyl ester.

5. The process as defined by claim 1, the catalytic amount being between about 0.1 and 0.5 mol per liter of reaction mixture.

6. The process as defined by claim 1, the carboxylic acid being selected from the group consisting of acetic, propionic, isobutyric, hexanoic, monochloroacetic, dichloroacetic, bromoacetic, α-chloropropionic, α-bromopropionic, acrylic, methacrylic, benzoic, toluic, naphthenic, succinic, adipic, phthalic, and α,α-dichloropropionic acid.

* * * * *